United States Patent [19]

Rosenberger et al.

[11] Patent Number: 4,623,745

[45] Date of Patent: Nov. 18, 1986

[54] PROCESS FOR PRODUCING PHENOLIC THIOCARBOXYLIC ESTERS

[75] Inventors: Siegfried Rosenberger, Riehen; Werner Stegmann, Liestal, both of Switzerland

[73] Assignee: Ciba-Geigy Corporation, Ardsley, N.Y.

[21] Appl. No.: 755,383

[22] Filed: Jul. 16, 1985

[30] Foreign Application Priority Data

Jul. 25, 1984 [CH] Switzerland .................. 3599/84

[51] Int. Cl.$^4$ ............................... C07C 149/40
[52] U.S. Cl. ...................................... 560/15
[58] Field of Search ......................... 560/15; 568/51

[56] References Cited

U.S. PATENT DOCUMENTS

| | | | |
|---|---|---|---|
| 2,417,118 | 3/1947 | McCleary | 568/51 |
| 3,553,270 | 1/1971 | Wollensak | 568/51 |
| 3,637,802 | 1/1972 | Eggensperger | 560/51 |
| 3,832,328 | 8/1974 | Eggensperger | 524/289 |
| 3,903,173 | 9/1975 | Eggensperger | 568/51 |
| 4,091,037 | 5/1978 | Arold | 568/51 |
| 4,304,940 | 12/1981 | Wedemeyer | 568/51 |

FOREIGN PATENT DOCUMENTS 1569743  6/1969  France ................... 568/51

*Primary Examiner*—Michael L. Shippen
*Attorney, Agent, or Firm*—Harry Falber

[57] ABSTRACT

Compounds of the formula I

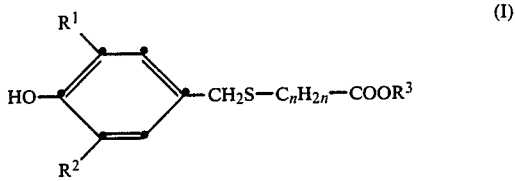
(I)

wherein $R^1$ and $R^2$ independently of one another are each tert-butyl, $R^3$ is $C_1$–$C_{20}$-alkyl, or $C_2$–$C_{20}$-alkyl interrupted by —O— or —S—, and n is the number 1 or 2, can be obtained, with a very high degree of yield and purity, by reaction of a phenol of the formula II

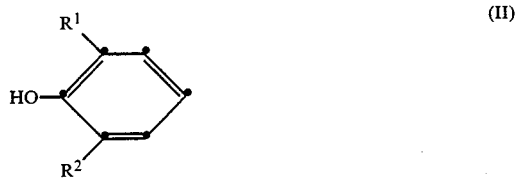
(II)

with formaldehyde and a mercaptan of the formula III

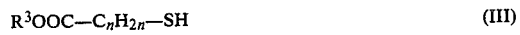

$R^3OOC-C_nH_{2n}-SH$ (III)

in the presence of catalytic amounts of a primary or secondary amine. Such compounds are stabilizers for organic materials.

8 Claims, No Drawings

PROCESS FOR PRODUCING PHENOLIC THIOCARBOXYLIC ESTERS

The present invention relates to a novel single-stage process for producing phenolic thiocarboxylic esters.

The production of phenolic thiocarboxylic esters in two stages, either by way of the Mannich base, or by reaction of corresponding phenols with mercapto acids and formaldehyde and subsequent esterification of the acids obtained, is known. It is described for example in the U.S. Pat. No. 3,832,328 and, as regards the Mannich reaction, also in the European Patent Application No. 59,168. These two-stage processes are however involved and therefore costly, and the yield and purity of the resulting products are unsatisfactory. U.S. Pat. No. 3,553,270 describes a single-stage process for producing phenolic thioethers by reaction of the corresponding phenol with formaldehyde and a mercaptan in the presence of a strong base, such as trimethylamine or particularly an alkali metal hydroxide, as catalyst. Attempts to produce also phenolic thiocarboxylic esters by this method have failed. It has however been found that, surprisingly, phenolic thiocarboxylic esters can be obtained with a high level of purity and yield by the use of primary or secondary amines as catalysts.

The present invention accordingly relates to a process for producing compounds of the formula I

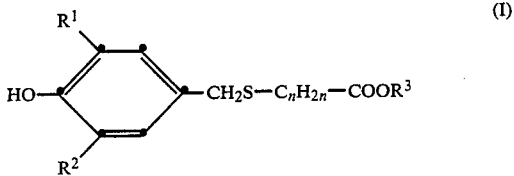

wherein $R^1$ and $R^2$ independently of one another are each tert-butyl, $R^3$ is $C_1$–$C_{20}$-alkyl, or $C_2$–$C_{20}$-alkyl interrupted by —O— or —S—, and n is the number 1 or 2, by reaction of a phenol of the formula II

with formaldehyde and a mercaptan of the formula III $$R^3OOC—C_nH_{2n}—SH \quad (III),$$

wherein $R^1$, $R^2$, $R^3$ and n have the meanings defined above, at a temperature of between 20° and 200° C. and in the presence of a catalyst, in which process the catalyst used is a primary or secondary amine of the formula IV

in which $R^4$ and $R^5$ independently of one another are each $C_2$–$C_{20}$-alkyl or hydroxyalkyl, $C_5$–$C_7$-cycloalkyl, phenyl or benzyl, and $R^5$ can additionally be hydrogen.

As $C_1$–$C_{20}$-alkyl, $R^3$ is for example: methyl, ethyl, propyl, isopropyl, n-butyl, sec-butyl, tert-butyl, pentyl, hexyl, n-octyl, 2-ethylhexyl, 1,1,3,3-tetramethylbutyl, nonyl, decyl, dodecyl, tridecyl, hexadecyl, octadecyl or eicosyl. The preferred meaning of $R^3$ is 2-ethylhexyl or iso-tridecyl (tridecyl isometric mixture).

Examples of $R^3$ as $C_2$–$C_{20}$-alkyl interrupted by —O— or —S— are: methoxymethyl, 2-ethoxyethyl, 2-n-butoxyethyl, 3-n-butoxyethyl, 2-octoxyethyl, 2-hexadecyloxyethyl, 2-ethoxymethyl, butoxymethyl, methoxypropyl, ethoxypropyl, 3-thiaheptyl or 3-thia-5-methylhexyl.

n is preferably 1.

As $C_2$–$C_{20}$-alkyl, $R^4$ and $R^5$ are for example: ethyl, propyl, isopropyl, n-butyl, sec-butyl, tert-butyl, pentyl, hexyl, octyl, decyl, dodecyl, hexadecyl, octadecyl or eicosyl; and, as $C_2$–$C_{20}$-hydroxyalkyl, they are: 2-hydroxyethyl, 3-hydroxypropyl, 3-hydroxybutyl, 8-hydroxyoctyl, 2-hydroxybutyl or 3-hydroxypentyl.

As $C_5$–$C_7$-cycloalkyl, $R^4$ and $R^5$ are for example: cyclopentyl, cycloheptyl and especially cyclohexyl.

$R^4$ and $R^5$ are preferably $C_2$–$C_8$-alkyl, and $R^5$ in addition also hydrogen. More especially preferred, $R^4$ and $R^5$ are identical and are particularly n-butyl.

The process according to the invention is performed especially advantageously by reaction of 1 mol of the phenol of the formula II with 1.0 to 2.0 mols of formaldehyde and 0.9 to 1.3 mols of a mercaptan of the formula III, in the presence of at least 0.5 mol %, relative to the phenol of the formula II, of the catalyst of the formula IV. There are preferably used 1 to 15 mol %, particularly 2.5 to 10 mol %, of catalyst, relative to the phenol.

The reaction can be carried out with or without solvent. Suitable solvents are those which have a certain solubility with respect to the reactants, but which are essentially inert under the reaction conditions. Examples of solvents suitable for this purpose are: hydrocarbons, such as toluene, xylene, octane and β-terpene; ethers, such as dioxane, diethyl ether, dimethyl ether of ethylene glycol, tetrahydrofuran, and so forth. Also chlorinated hydrocarbons, such as carbon tetrachloride, chloroform, trichloroethane and perchloroethylene, can advantageously be used. Other suitable solvents are for example: dimethylformamide, dimethylacetamide or dimethyl sulfoxide. Also primary or secondary alcohols having 3 to 6C atoms, such as isopropanol, sec-butyl alcohol, tert-butyl alcohol, tert-amyl alcohol and hexyl alcohol, can be recommended for a successful carrying out of the process according to the invention.

The formaldehyde can be in the form of an aqueous solution, especially an approximately 35% aqueous solution, or in the form of paraformaldehyde. When paraformaldehyde is used, it is necessary to add the 5- to 20-fold amount, preferably the 8- to 12-fold amount, in weight, relative to the paraformaldehyde, of a depolymeriser, for example dimethylformamide, dimethylacetamide or dimethyl sulfoxide.

The reaction temperature varies depending on the reactant. Suitable temperatures are between 20° and 200° C. A preferred temperature range is between 80° and 140° C. It proves advantageous in practice to perform the process at the boiling temperature of the reaction mixture. Accordingly, the temperature range of between 80° C. and the boiling temperature of the reaction mixture is particularly preferred.

The duration of the reaction is likewise dependent on the reactants; in general, the reaction is finished after 4 to 8 hours. Isolation of the final product is effected by customary separation of the volatile constituents, for example by distillation in vacuo, or by the dissolving out of optionally nonvolatile amine catalyst residues with dilute acid, for example dilute hydrochloric acid or sulfuric acid. On account of the high degree of purity of the product obtained, no additional purification is necessary.

The compounds of the formula I are valuable stabilisers for organic materials which are subject to degradation by light, heat or oxygen; they are valuable stabilisers in particular for elastomers and lubricants.

The following Examples further illustrate the present invention without limiting the scope thereof.

EXAMPLE 1

A mixture of 206 g of 2,6-di-tert-butylphenol, 45 g of paraformaldehyde, 204 g of thioglycolic acid-2-ethyl-n-hexyl ester, 7.6 g of di-n-butylamine and 150 ml of dimethylformamide is stirred at about 120° C. for 3 to 4 hours under refluxing conditions and with the feeding in of nitrogen. The volatile constituents (residual aldehyde, di-n-butylamine and dimethylformamide) are subsequently completely removed by being distilled off in vacuo. There are thus obtained 415 g (98% of theory) of 3,5-di-tert-butyl-4-hydroxybenzylmercaptoacetic acid-2-ethyl-n-hexyl ester in the form of a viscous pale-yellow oil, which, on standing in the cold, solidifies in the crystalline state (m.p. 20° C.). Without further purification steps, the product is shown to be very pure (content >98%) after verification by thin-layer chromatography, NMR and phenol titration.

EXAMPLES 2-4

When in Example 1 the thioglycolic acid-2-ethyl-n-hexyl ester is replaced in each case by the equivalent amount of one of the homologous thioglycol esters of the formula

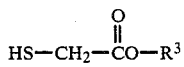

wherein $R^3$ has the meaning given in the following Table, there are obtained, with otherwise an analogous procedure, the corresponding homologous phenols with practically the same level of purity and yield.

| Example | $R^3$ | Aspect |
|---|---|---|
| 2 | n-$C_8H_{17}$ | crystalline, m.p. 35° C. |
| 3 | n-$C_{12}H_{25}$ | viscous oil |
| 4 | iso-$C_{13}H_{27}$ | viscous oil |

EXAMPLE 5

By using in Example 1, in place of dimethylformamide, the equivalent amount of dimethylacetamide (as depolymeriser of the paraformaldehyde), there is obtained, with otherwise the same procedure, the product of Example 1 in a similar quality and yield.

EXAMPLE 6

If there is used in Example 1, instead of paraformaldehyde, the aliquot amount of formaldehyde in the form of a 35% aqueous solution, the addition of dimethylformamide being dispensed with, there is obtained within 7 to 8 hours reaction time at about 100° C., with otherwise the same procedure, the product of Example 1 in similar quality and yield.

EXAMPLE 7

When in Example 1 the di-n-butylamine is replaced by the equivalent amount of n-octylamine, there is obtained, the procedure otherwise being analogous, the product of Example 1 with a similar degree of yield and purity.

What is claimed is:

1. A process for producing a compound of the formula I

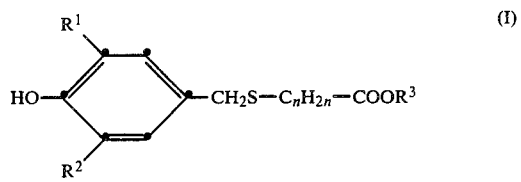

wherein $R^1$ and $R^2$ independently of one another are each tert-butyl, $R^3$ is $C_1$–$C_{20}$-alkyl interrupted by —O— or —S—, and n is the number 1 or 2, by reaction of a phenol of the formula II

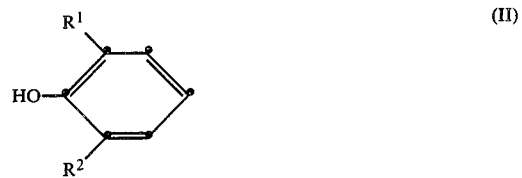

with formaldehyde and a mercaptan of the formula III

wherein $R^1$, $R^2$, $R^3$ and n have the meanings defined above, at a temperature of between 20° and 200° C. and in the presence of a catalyst, in which process the catalyst used is a primary or secondary amine of the formula IV

in which $R^4$ and $R^5$ independently of one another are each $C_2$–$C_{20}$-alkyl or hydroxyalkyl, $C_5$–$C_7$-cycloalkyl, phenyl or benzyl, and $R^5$ can additionally be hydrogen.

2. A process according to claim 1 for producing a compound of the formula I wherein $R^1$ and $R^2$ independently of one another are each tert-butyl, and $R^3$ is $C_4$–$C_{13}$-alkyl.

3. A process according to claim 2 for producing a compound of the formula I wherein n is the number 1.

4. A process according to claim 1 for producing 3,5-di-tert-butyl-4-hydroxybenzylmercaptoacetic acid-2-ethyl-n-hexyl ester.

5. A process according to claim 1 for producing 3,5-di-tert-butyl-4-hydroxybenzylmercaptoacetic acid-isotridecyl ester.

6. A process according to claim 1, which process comprises reacting 1 mol of the phenol of the formula II with 1.0 to 2.0 mols of formaldehyde and 0.9 to 1.3 mols of a mercaptan of the formula III in the presence of at least 0.5 mol %, relative to the phenol of the formula II, of the catalyst of the formula IV.

7. A process according to claim 1, wherein there is used a catalyst of the formula IV in which $R^4$ and $R^5$ are $C_2$–$C_8$-alkyl, and $R^5$ can additionally be hydrogen.

8. A process according to claim 1, wherein the catalyst used is di-n-butylamine.

* * * * *